United States Patent
Harshman et al.

(10) Patent No.: US 7,530,953 B2
(45) Date of Patent: May 12, 2009

(54) ELECTRICAL CONNECTOR

(75) Inventors: E. Scott Harshman, Kirkland, WA (US); Donald Masters, Fremont, CA (US); Peter Thornton, Los Altos, CA (US)

(73) Assignee: Boston Scientific Neuromodulation Corporation, Maple Grove, MN (US)

( * ) Notice: Subject to any disclaimer, the term of this patent is extended or adjusted under 35 U.S.C. 154(b) by 0 days.

(21) Appl. No.: 11/669,752

(22) Filed: Jan. 31, 2007

(65) Prior Publication Data

US 2007/0178717 A1 Aug. 2, 2007

Related U.S. Application Data

(62) Division of application No. 11/343,801, filed on Jan. 30, 2006.

(51) Int. Cl.
*A61B 5/02* (2006.01)
*A61B 5/04* (2006.01)

(52) U.S. Cl. .................. 600/463; 600/381; 600/486; 600/505

(58) Field of Classification Search .......... 600/505, 600/463, 381, 394, 481, 459, 486; 439/909, 439/53, 660
See application file for complete search history.

(56) References Cited

U.S. PATENT DOCUMENTS

| | | | |
|---|---|---|---|
| 4,243,884 A | 1/1981 | Avera, Jr. | |
| 4,362,166 A * | 12/1982 | Furler et al. | 600/483 |
| 4,407,298 A * | 10/1983 | Lentz et al. | 600/526 |
| 5,150,715 A | 9/1992 | Ishiguro et al. | |
| 5,178,159 A | 1/1993 | Christian | |
| 5,348,481 A | 9/1994 | Ortiz | |
| 5,353,798 A | 10/1994 | Sieben | |
| 5,383,460 A | 1/1995 | Jang et al. | |
| 5,715,825 A | 2/1998 | Crowley | |
| 5,902,245 A * | 5/1999 | Yock | 600/463 |
| 5,957,941 A | 9/1999 | Ream | |
| 5,971,923 A | 10/1999 | Finger | |

(Continued)

FOREIGN PATENT DOCUMENTS

EP 1026982 11/2005
WO WO 2006026439 3/2006

OTHER PUBLICATIONS

Universal Serial Bus Specification Revision 2.0, Apr. 27, 2000, Compaq, Hewlett-Packard, Intel, Lucent, Microsoft, NEC, Philips. pp. 1-650.

(Continued)

*Primary Examiner*—Douglas W. Owens
*Assistant Examiner*—Chuc Tran
(74) *Attorney, Agent, or Firm*—Darby & Darby P.C.

(57) ABSTRACT

An electrical connector is described. In one implementation, the connector includes a female portion including one or more electrical contacts and a male portion including one or more electrical contacts. The female portion and the male portion each have a self-orientating geometry that allows the male portion to be mated with the female portion in any rotational position along 360 degrees of rotation. When mated, the electrical contacts of the female portion mate with corresponding one or more electrical contacts of the male portion to form one or more electrical connections between two electronic components.

11 Claims, 5 Drawing Sheets

U.S. PATENT DOCUMENTS

| | | | |
|---|---|---|---|
| 6,050,949 | A | 4/2000 | White et al. |
| 6,244,882 | B1 | 6/2001 | Greenstein |
| 6,264,613 | B1 * | 7/2001 | Pfeiffer et al. ............. 600/505 |
| 6,309,358 | B1 | 10/2001 | Okubo |
| 6,319,227 | B1 * | 11/2001 | Mansouri-Ruiz |
| 6,461,199 | B1 * | 10/2002 | Koga et al. ................ 439/668 |
| 6,485,482 | B1 | 11/2002 | Belef |
| 6,508,781 | B1 | 1/2003 | Brennan et al. |
| 6,530,887 | B1 | 3/2003 | Gilbert et al. |
| 6,714,809 | B2 | 3/2004 | Lee et al. |
| 6,770,058 | B1 | 8/2004 | Liprie |
| 6,814,727 | B2 | 11/2004 | Mansouri-Ruiz |
| 7,004,787 | B2 | 2/2006 | Milan |
| 2002/0072704 | A1 | 6/2002 | Mansouri-Ruiz |
| 2003/0073348 | A1 | 4/2003 | Ries et al. |
| 2003/0143895 | A1 | 7/2003 | Sommer et al. |
| 2004/0230123 | A1 | 11/2004 | White et al. |
| 2005/0043618 | A1 | 2/2005 | Mansouri-Ruiz |
| 2005/0251035 | A1 | 11/2005 | Wong et al. |
| 2007/0178768 | A1 * | 8/2007 | Harshman et al. .......... 439/660 |

OTHER PUBLICATIONS

Errata for "USB Revision 2.0 Apr. 27, 2000" as of May 28, 2002, 7 pages. http://www.usb.org.
USB 2.0 Specification Engineering Change Notice (ECN) #1: Mini-B connector Oct. 20, 2000.
Errata for "USB Revision 2.0 Apr. 27, 2000" as of Dec. 7, 2000 pp. 1-31. http://www.usb.org.
USB Engineering Change Notice: "Interface Association Descriptors," Applies to: USB Specification, Revision 2.0 pp. 1-5.
On-The-Go Supplement to the USB 2.0 Specification Revision 1.0a Jun. 24, 2003.
Showing Changes Made/Marked Version: On-The-Go Supplement to the USB 2.0 Specification Revision 1.0a Jun. 24, 2003.
Errata for "On-The-Go Supplement to the USB 2.0 Specification," Revision 1.0a, Jan. 27, 2004.
USB Engineering Change Notice: "Pull-up/pull-down resistors," Applies to: USB Specification Revision 2.0.
USB Engineering Change Notice: "Rounded Chamfer," Applies to: USB 2.0 Specification.
USB Engineering Change Notice: "Unicode UTF-16LE for String Descriptors," Applies to: USB Specification, Revision 2.0, Feb. 21, 2005.
Universal Serial Bus Specification Revision 2.0, Apr. 27, 2000, Compaq, Hewlett-Packard, Intel, Lucent, Microsoft, NEC, Philips. pp. 1-650.
Errata for "USB Revision 2.0 Apr. 27, 2000" as of May 28, 2002, 7 pages. http://www.usb.org.
USB 2.0 Specification Engineering Change Notice (ECN) #1: Mini-B connector Oct. 20, 2000.
Errata for "USB Revision 2.0 Apr. 27, 2000" as of Dec. 7, 2000 pp. 1-31.
USB Engineering Change Notice: "Interface Association Descriptors, " Applies to: USB Specification, Revision 2.0 pp. 1-5. Apr. 27, 2000.
On-The-Go Supplement to the USB 2.0 Specification Revision 1.0a Jun. 24, 2003.
Showing Changes Made/Marked Version: On-The-Go Supplement to the USB 2.0 Specification Revision 1.0a Jun. 24, 2003.
Errata for "On-The-Go Supplement to the USB 2.0 Specification, " Revision 1.0a, Jan. 27, 2004.
USB Engineering Change Notice: "Pull-up/pull-down resistors, " Applies to: USB Specification Revision 2.0. Jan. 27, 2004.
USB Egineering Change Notice: "Rounded Chamfer," Applied to: USB 2.0 Specification. Jan. 27, 2004.
USB Engineering Change Notice: "Unicode UTF-16LE for String Descriptors," Applies to: USB Specification, Revision 2.0, Feb. 21, 2005.

* cited by examiner

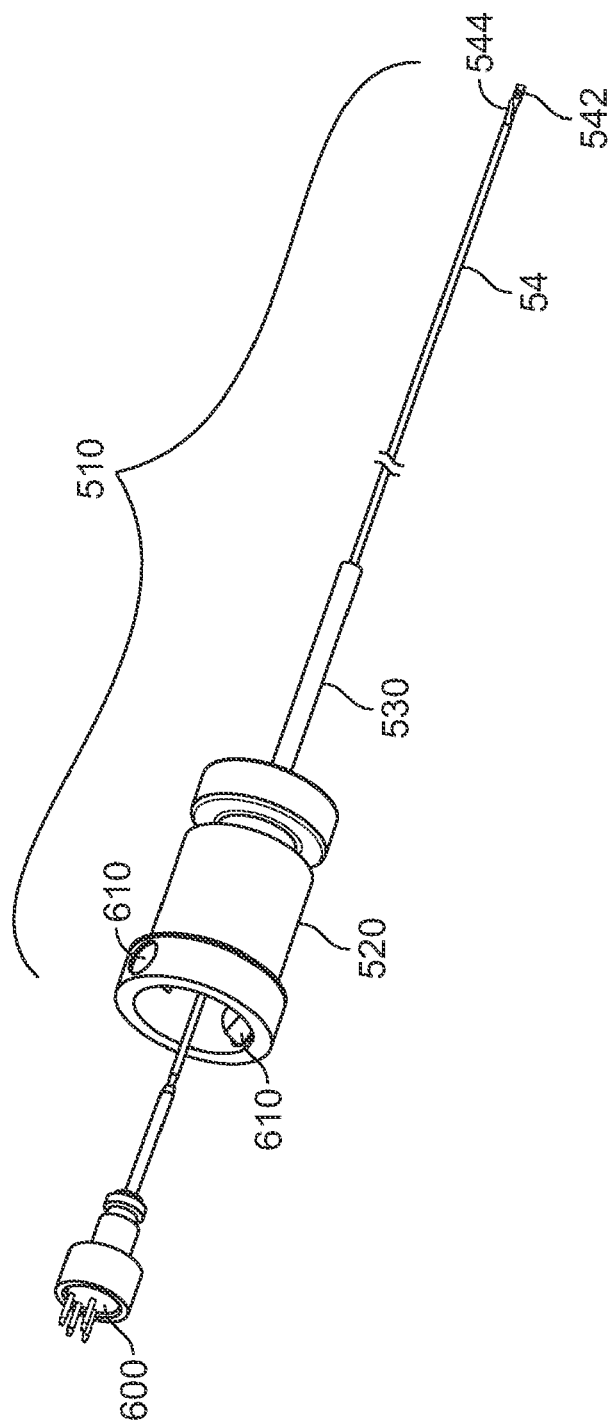
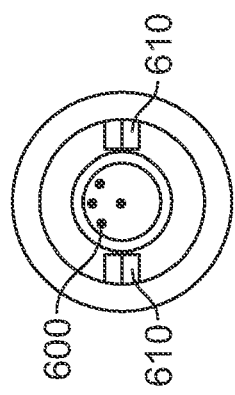
FIG. 6A
FIG. 6B

ELECTRICAL CONNECTOR

CROSS-REFERENCE TO RELATED APPLICATIONS

This application is a divisional application of and claims priority to pending U.S. application Ser. No. 11/343,801, entitled "ELECTRICAL CONNECTOR", filed on Jan. 30, 2006, the entire contents of which are hereby incorporated by reference.

TECHNICAL FIELD

This invention relates to electrical connectors.

BACKGROUND

Electrical connectors come in various forms and serve various purposes. For example, computers are commonly connected to peripheral devices (e.g., keyboards, monitors and printers) through USB (Universal Serial Bus) connectors and multi-pin connectors. An RJ-11 phone plug type connector is also used in computer networks, as well as other implementations. For example, a catheter including a device such as an ultrasonic imaging device requiring rotation during operation may be mechanically and electrically connected to a motor drive unit. An RJ-11 connector coupled with a rotary transformer can be used to connect the motor drive unit to the catheter. Typically, an electrical connector has a female portion and a male portion that can be mated to form an electrical connection between the two portions. A conventional USB connector, for example, requires the male portion be inserted into the female portion at one particular orientation along 360 degrees of rotation.

SUMMARY

This invention relates to electrical connectors. In general, in one aspect, the invention features an apparatus including a connector that electrically connects an electronic component with an imaging catheter. The connector includes a female portion including one or more electrical contacts and a male portion including one or more electrical contacts. The female portion and the male portion each have a self-orientating geometry that allows the male portion to be mated with the female portion in any rotational position along 360 degrees of rotation. When mated, the electrical contacts of the female portion mate with corresponding one or more electrical contacts of the male portion to form one or more electrical connections between the electronic component and the imaging catheter.

Implementations of the apparatus may include one or more of the following features. The electronic component can be a motor drive unit for driving an ultrasound transducer included in the imaging catheter. The electrical contacts on the male portion can be shaped as a series of axially stacked rings and the electrical contacts on the female portion can be shaped as fingers spaced around a circumference of the female portion and axially offset from one another. The male and female portions are configured to mate such that each finger is in contact with a corresponding one of the rings. The fingers can have a spring force that causes the fingers to press against the rings when the male and female portions are mated. Each finger can have a ridged portion along the length of the finger and the ridged portion of the finger can come into contact with the corresponding ring. The female portion can include an outer shield configured to shield the electrical contacts from radio frequency signals. In one implementation, the connector can conform to the USB (Universal Serial Bus) electrical specification and protocol.

In general, in another aspect, the invention features an imaging system. The imaging system includes an imaging catheter, a motor drive unit and a connector. The imaging catheter includes a rotator core, a drive shaft, and an imaging core, and is configured to electrically connect to a motor drive unit by a connector, where a female or male portion of the connector is included within the rotator core. The motor drive unit is configured to electrically connect to the imaging catheter by the connector and to provide rotational movement to the imaging core, where a female or male portion of the connector is included at a distal end of the motor drive unit. The connector is configured to electrically connect the imaging catheter to a motor drive unit. The connector includes a female portion including one or more electrical contacts and a male portion including one or more electrical contacts. The connector is rotatable and the male portion and the female portion each have a corresponding locking geometry that allows for transfer of rotational movement between the male and female portions when mated. One of either the male or female portion of the connector is included at the distal end of the motor drive unit and the corresponding portion is included within the rotator core of the imaging catheter.

Implementations of the system may include one or more of the following features. The locking geometry can include one or more keys included in one of the male or female portions and one or more corresponding grooves included in the other of the male or female portions. The electrical contacts on the male portion can be shaped as a series of axially stacked rings. The electrical contacts on the female portion can be shaped as fingers spaced around a circumference of the female portion and axially offset from one another. The male and female portions are configured to mate such that each finger is in contact with a corresponding one of the rings. The fingers can have a spring force that urges the fingers to press against the rings when the male and female portions are mated. Each finger can have a ridged portion along the length of the finger and the ridged portion of the finger can come into contact with the corresponding ring. In one implementation, the connector can conform to the USB (Universal Serial Bus) electrical specification and protocol.

In general, in another aspect, the invention features an apparatus including a connector. The connector includes a female portion including one or more electrical contacts and a male portion including one or more electrical contacts. The female portion and the male portion each have a self-orientating geometry that allows the male portion to be mated with the female portion in any rotational position along 360 degrees of rotation. When mated, the electrical contacts of the female portion mate with corresponding one or more electrical contacts of the male portion to form one or more electrical connections.

Implementations of the apparatus may include one or more of the following features. The electrical contacts on the male portion can be shaped as a series of axially stacked rings. The electrical contacts on the female portion can be shaped as fingers spaced around a circumference of the female portion and axially offset from one another. When the male and female portions are mated, each finger is in contact with a corresponding one of the rings. The fingers can include a spring force that urges the fingers to press against the rings when the male and female portions are mated. Each finger can have a ridged portion along the length of the finger and the ridged portion of the finger comes into contact with a corresponding ring. The female portion can include an outer shield that shields the electrical contacts from radio frequency signals. In one implementation, the connector can conform to the USB (Universal Serial Bus) electrical specification and protocol.

In general, in another aspect, the invention features an apparatus including a connector. The connector is configured to connect a motor drive unit to a catheter, the catheter being a tubular instrument that can be inserted into a body cavity or blood vessel. The connector includes a female portion, including one or more electrical contacts and a locking geometry, where the one or more electrical contacts are configured to mate to one or more electrical contacts of a male portion and the locking geometry is configured to mate to a corresponding locking geometry of the male portion. The connector further includes a male portion, including one or more electrical contacts and a locking geometry, where the one or more electrical contacts are configured to mate to one or more electrical contacts of the female portion and the locking geometry is configured to mate to a corresponding locking geometry of the female portion. The connector is configured to rotate such that when the female and male portions are mated, rotational movement from the motor drive unit is transferred to the catheter and an electrical connection is made between the motor drive unit and the catheter.

Implementations of the apparatus can include one or more of the following features. The locking geometry can include one or more keys in either the female or male portion and one or more corresponding grooves in the other portion. The catheter can include a rotator core, a drive shaft, and an imaging core. The connector can be positioned within the rotator core. The electrical contacts on the male portion can be shaped as a series of axially stacked rings, and the electrical contacts on the female portion can be shaped as fingers spaced around a circumference of the female portion and axially offset from one another. When the male and female portions are mated, each finger is in contact with a corresponding one of the rings. The fingers can include a spring force that urges the fingers to press against the rings when the male and female portions are mated. Each finger can have a ridged portion along the length of the finger and the ridged portion of the finger comes into contact with a corresponding ring. In one implementation, the connector can conform to the USB (Universal Serial Bus) electrical specification and protocol. In another implementation, the connector can be a multi-pin connector and the male portion can include a plurality of pins and the female portion can include a plurality of corresponding apertures configured to receive the plurality of pins.

A connector implemented according to the invention can realize one or more of the following advantages. The male and female portions of the connector can be mated at any orientation, facilitating connection by a user. By eliminating the need for an "orientation zone", such a connector can be more compact than other types of connectors. The connector can accommodate a larger number of electrical contacts and can reduce noise better than other types of connector. The configuration of electrical contacts allows the connector to be included in a rotating housing, ideal for uses such as the catheter described without requiring a rotary transformer.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A and 6B illustrate a connector in a medical imaging catheter.

Like reference symbols in the various drawings indicate like elements.

DETAILED DESCRIPTION

Figure 1:
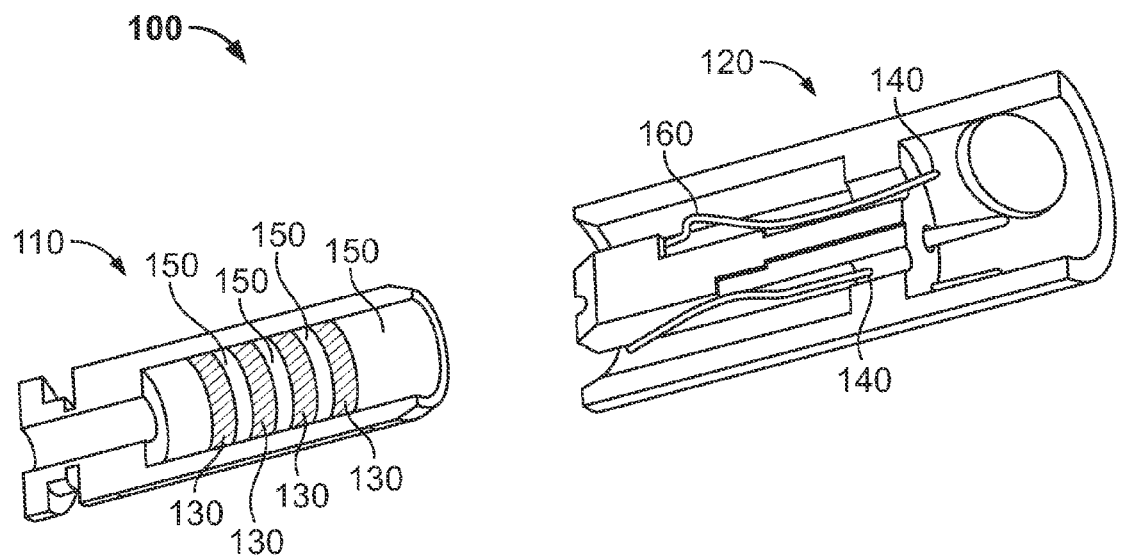
FIG. 1 illustrates a partial cut view of an orientation free connector.

FIG. 1 shows an orientation free connector 100 including a male portion 110 and a mating female portion 120. The male portion 110 includes a set of electrical contacts 130. The female portion 120 includes a corresponding set of electrical contacts 140. When the female portion of the connector is mated with the male portion, an electrical connection is established between each electrical contact on the male portion and the corresponding electrical contact on the female portion.

The electrical contacts 130, 140 can be made of any conductive material, for example, gold. Alternatively, the electrical contacts can be made of a non-conductive material that is coated in a conductive material. The electrical contacts 130, 140 have a self-orientating geometry that allows the male and female portions 110, 120 to be mated in any rotational position along 360 degrees of rotation, while still providing sufficient contact between the corresponding electrical contacts and while avoiding contact between electrical contacts that are intended to be connected. In general, there can be a one-to-one relationship in the connection of the electrical contacts 130 and 140.

In the example embodiment illustrated in FIG. 1, the electrical contacts 130 on the male portion 110 are shaped as a series of axially stacked rings. The contact rings are supported by an insulating layer 150. The insulating layer 150 can be made of any non-conductive material, e.g., a dielectric, for example, a plastic. Each electric contact 130 can be connected to wires or lead traces in the dielectric 150, e.g., in grooves formed therein. The wires or leads provide an electrical connection between the electric contacts 130 in the male portion (i.e., the rings) and an electrical component attached to the connector (e.g., a power supply or motor drive unit). The dielectric 150 also provides support for an outer shield that can shield the rings from RF (radio frequency) signals.

The electrical contacts 140 on the female portion 120 are shaped as a series of fingers spaced circumferentially about an inner region of the female portion 120 and axially offset from another. Each finger has a ridged portion 160 along the length of the finger. The ridged portion 160 is positioned such that when the male and female portions of the connector are mated, the ridged portion 160 of the finger contacts a ring in the male portion 110. The position of the ridge along the longitudinal axis of the female portion 120 varies from finger to finger. This allows each finger of the female portion 120 to contact a different ring of the male portion 110.

The fingers can have a degree of flexibility and resilience. When the male portion 110 of the connector is inserted into the female portion 120, the fingers on the female portion 120 bend to allow the male portion 110 to pass over the fingers. At the same time, the resilience or spring force of the fingers tends to urge the fingers into contact with the rings of the male portion 110, once the male portion 110 is engaged in the female portion 120.

In the embodiment shown in FIG. 1, each portion of the connector 100 includes a set of four electrical contacts. Other embodiments can include other numbers of electrical contacts, for example, one or more. The number of contacts and the spacing of the contacts on the female portion 120 correspond to the number and spacing on the male portion 110.

In some applications, a connection is required between two components that rotate during operation. One approach is to connect the two components using a non-rotating electrical connector (e.g., an RJ-11 connector) in conjunction with a separate rotary transformer. However, this approach requires use of the separate rotary transformer, adding bulk and expense to the electrical connector.

Figure 2:
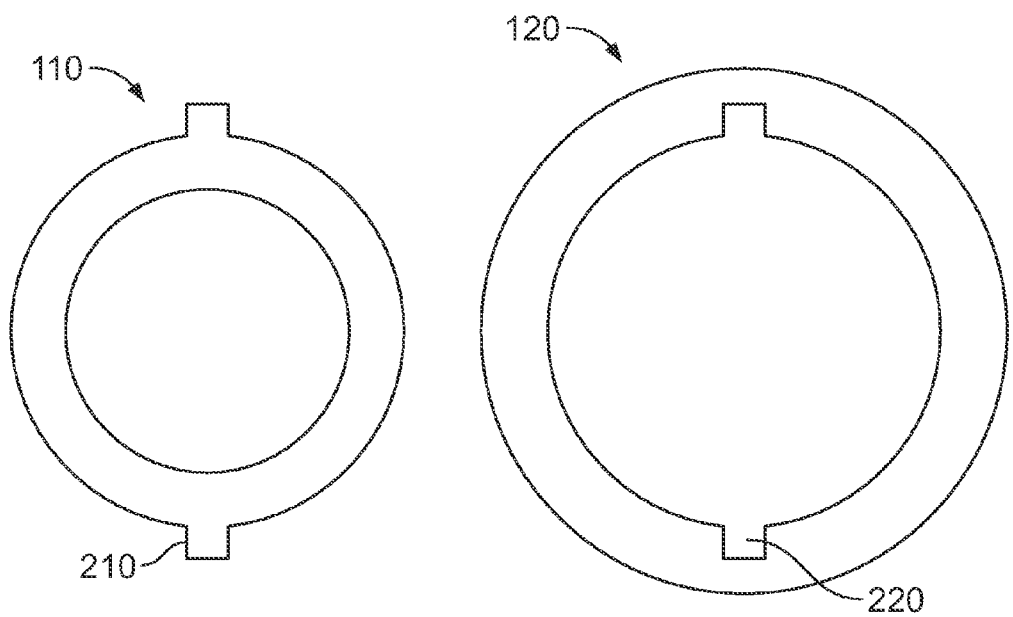
FIG. 2 illustrates a cross-sectional views of male and female portions of a rotatable connector.

The connector described herein can rotate without requiring a separate rotary transformer. A rotating connector can include a positive locking geometry that allows for transfer of rotational movement between the male and female portions. For example, as illustrated in FIG. 2, the locking geometry can include a set of keys 210 on the male portion 110 that fit into a corresponding set of grooves 220 on the female portion 120. Although only two keys and grooves are shown, more or fewer keys and grooves can be used. In embodiments where the connector 100 includes the keyed geometry, the housing 200 is not orientation free. For example, in the embodiment shown in FIG. 2, there are only two rotational positions along 360 degrees of rotation where the keys and grooves can be aligned.

In another embodiment, the connector 100 is configured for mounting to a panel, for example, a panel on the front or back of a computer. That is, the female portion 120 can be affixed within the panel, and the male portion 110 can be attached to the distal end of an electrical cable affixed to a peripheral device, e.g., a keyboard. In another embodiment, the connector 100 can be configured to provide a liquid tight seal around the electrical contacts. For example, the male portion 110 can include an o-ring held within a groove located at the distal end of the male portion 110. When the male portion 110 is inserted into the female portion 120, the o-ring forms a liquid tight seal.

A USB connector generally refers to a connector meeting the Universal Standard Bus (USB) Specification. The USB Specification includes a mechanical specification, an electrical specification and a USB protocol. The USB Specification sets a standard to ensure consistency and connectivity among various USB devices and host devices. In one implementation, the connector 100 described herein can be configured to conform to the USB Specification other than the physical configuration of the connector itself. That is, the connector 100 can conform to the electrical specification and USB protocol set forth in the USB Specification Revision 2.0, dated Apr. 27, 2000, the entire contents of which are hereby incorporated herein by reference, or other versions of the USB Specification. The connector 100 does have a different physical configuration then a standard USB connector, and is not configured to mate with either a male or female standard USB connector. For certain applications where an orientation free connector or a rotatable connector is desirable, a standard USB connector could be replaced by a connector conforming to the USB specification electronically, but physically configured as described above in reference to FIG. 1.

Figure 3:
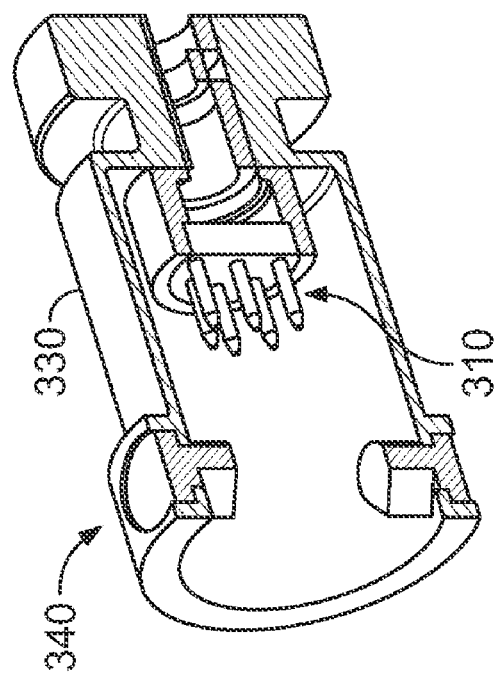
FIG. 3 illustrates a rotatable multi-pin connector.
Figure 3:
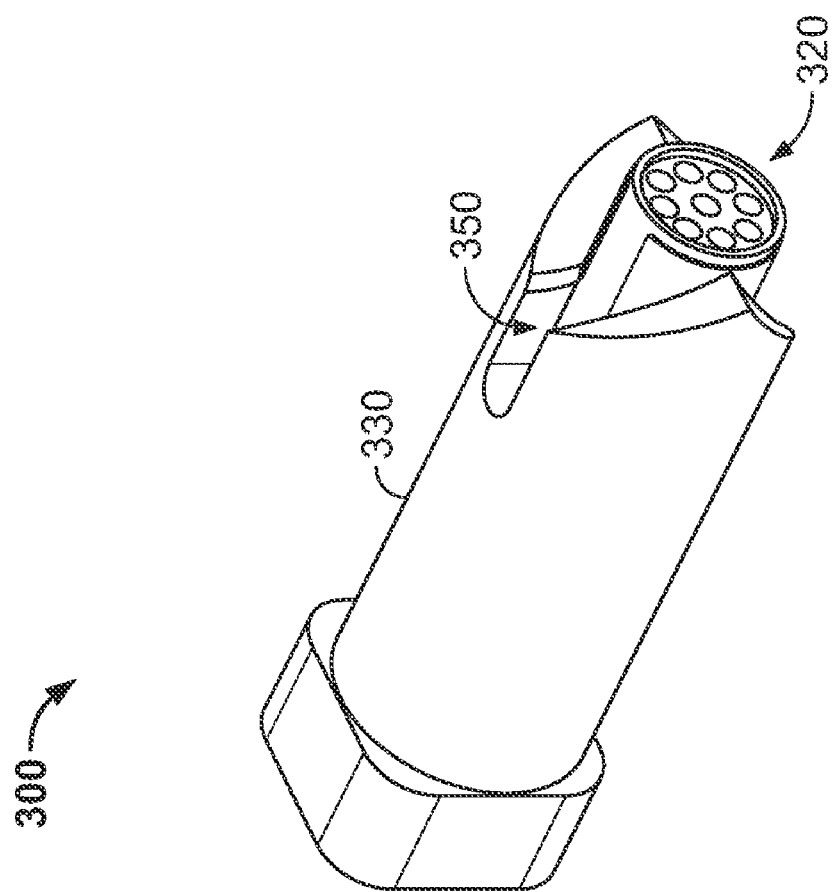

One or more of the above-described features can also be used with other configurations of connectors. For example, FIG. 3 illustrates a multi-pin connector 300 that can rotate. The multi-pin connector has a male connector 310 and a female connector 320, each encased within a housing 330. The housing 330 can include positive locking geometry that allows for transfer of rotational movement between the male and female connectors 310, 320. In the implementation shown, the positive locking geometry is a set of keys 340 that can slide into a corresponding set of grooves 350.

Figure 4:
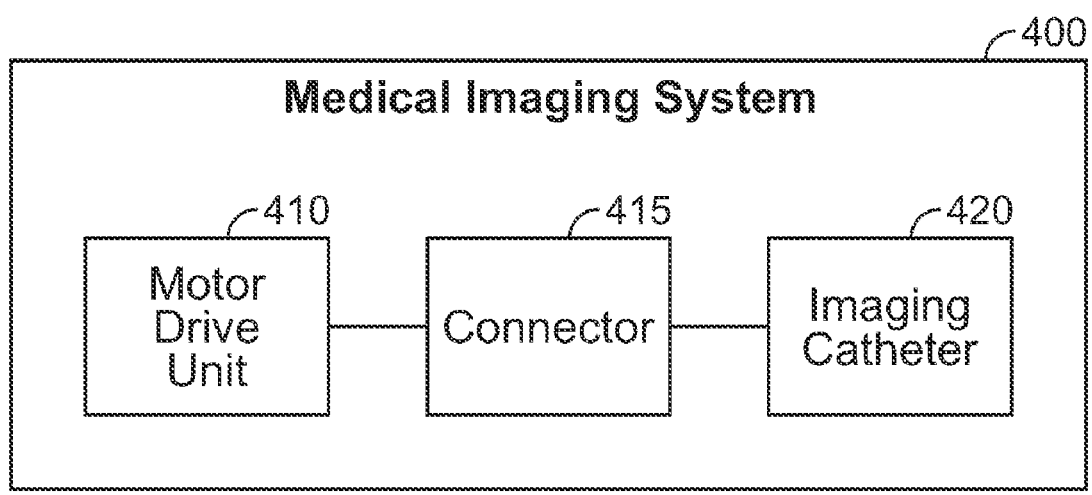
FIG. 4 is a schematic representation of a medical imaging system.

The above-described connectors can be used in a variety of contexts. An exemplary medical imaging system 400 is illustrated in FIG. 4. A connector 415 configured as one of the connectors described herein can be used in the medical imaging system 400 to connect a motor drive unit 410 to a medical imaging catheter 420. The motor drive unit 410 can provide power, data transfer capabilities, and/or mechanical drive to the medical imaging catheter 420.

The medical imaging catheter 420 can be used in a variety of medical procedures. One such procedure is IVUS (Intravascular Ultrasound) imaging. IVUS is a medical imaging technique that creates images of the interior of a blood vessel by inserting an imaging catheter into the blood vessel. An ultrasound transducer mounted at the tip of the catheter interrogates the cross-sectional plane of the blood vessel by rotating and then emitting ultrasonic pulses and receiving echoes of the emitted pulses at various angular positions. An image processor draws radial lines corresponding to each angular position. The image processor assigns brightness values to pixels on the line based on the echo received for that angular position. The drawing of a large number of such radial lines results in an IVUS image.

Figure 5A:
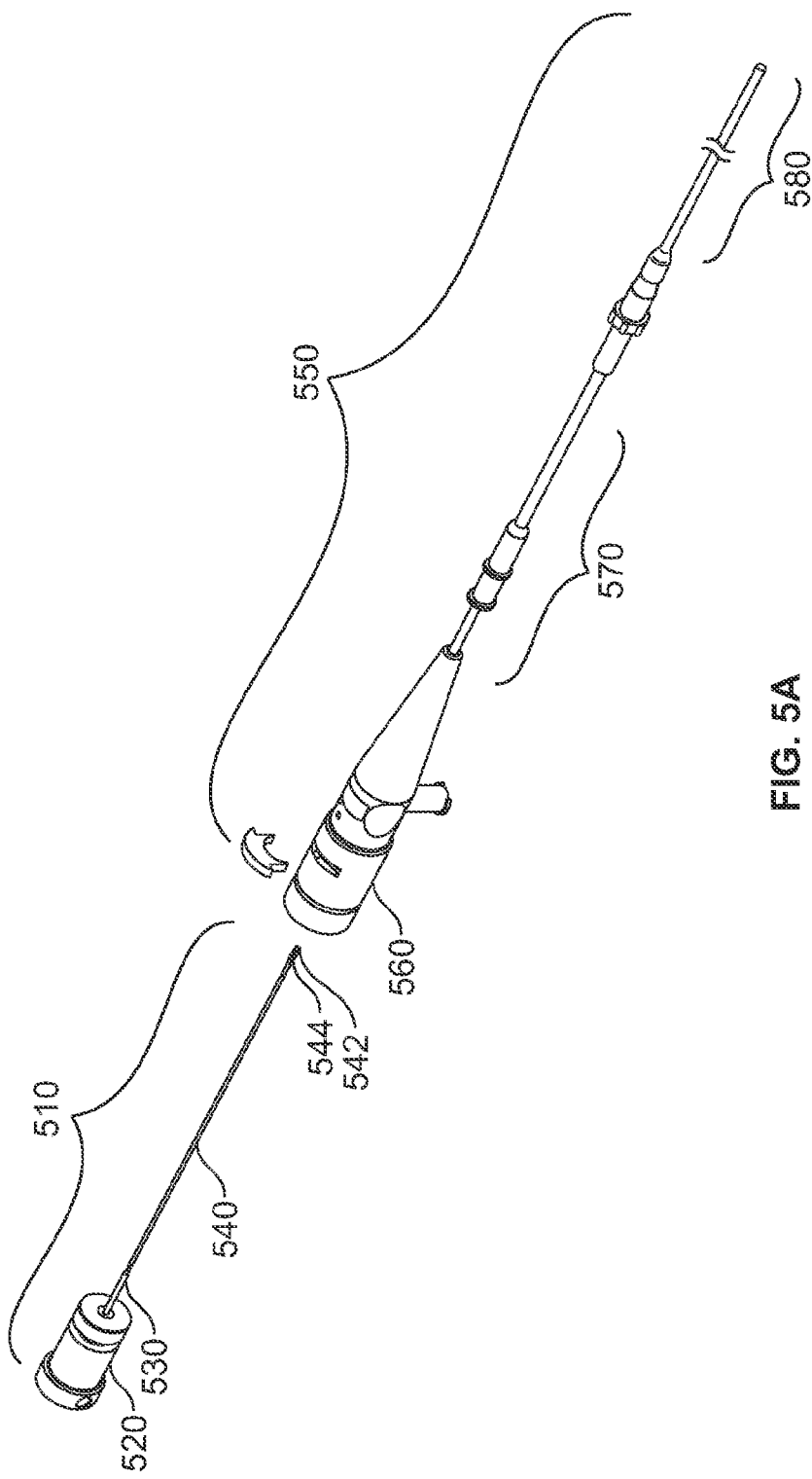
FIGS. 5A and 5B illustrate a medical imaging catheter.

FIG. 5A illustrates one embodiment of a medical imaging catheter 420 for performing IVUS imaging. In this embodiment, the catheter includes a first subassembly 510 and a second subassembly 550. The first subassembly includes a rotator core 520, a drive shaft 530, and an imaging core 540. At the distal end of the imaging core 540 is an ultrasound transducer 542 and an MPS (medical positioning sensor) coil 544 for tracking the movement of the imaging core 540. Inside of the rotator core 520 is an electrical connector 600, which is described in more detail below with reference to FIGS. 6A and 6B.

As shown in FIGS. 6A and 6B, an electrical connector 600 is located at the proximal end of the first subassembly 510. In the embodiment shown the electrical connector 600 is multi-pin connector similar to the multi-pin connector 300 described in reference to FIG. 3. In another embodiment, the connector 100 described in reference to FIG. 1 can be included in the proximal end of the first subassembly 510. The electrical connector 600 allows the catheter to be connected to another electrical component, e.g., a motor drive unit that provides power, data transfer capabilities, and mechanical drive to the catheter.

The electrical connector 600 can be secured inside the rotator core 520 by any means. FIG. 6 shows a pair of bolts 610 that are rotationally fixed with respect to connector 600. the bolts serve as an alignment feature when used in conjunction with the mating connector. The bolts can also function as the positive locking mechanism that allows for transfer of rotational movement. Alternatively, the rotator core 530 can include a separate positive locking mechanism.

The connector 600 can be a multi-pin connector or a connector including an axial ring configuration as described above. In the case where a multi-pin connector is used, the male portion of the multi-pin connector can only be inserted into the female portion at particular rotational positions. Thus, the multi-pin connector typically includes an orientation zone where the male portion can align itself with the female portion prior to insertion. The orientation free connector 100 shown in FIG. 1, by contrast, does not require an orientation zone because the male portion can be inserted into the female portion at any rotational position. Thus, the orientation free connector 100 is typically more compact in size than a multi-pin connector and can accommodate a larger number of electrical contacts than a multi-pin connector. The connector 100 typically has better shielding than a multi-pin connector and therefore, is better at reducing noise.

Figure 5B:
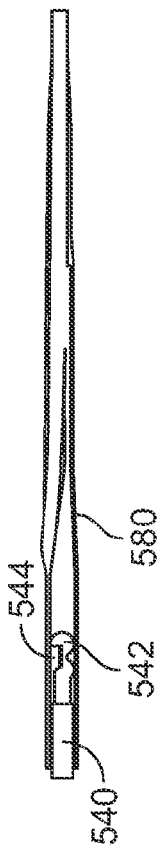

Referring back to FIG. 5A, the second subassembly 550 of the catheter includes a proximal housing 560, a telescope 570, and a sheath 580. To position the catheter for use, the sheath 580 is inserted into a patient's blood vessel. The first subassembly 510 is inserted into the second subassembly 550 such that the rotator core 520 and electrical connector 600 are positioned inside the proximal housing 560 and the imaging core 540, transducer 542 and MPS coil 544 are positioned inside the sheath 580. FIG. 5B shows the sheath 580 with the imaging core 540, transducer 542 and MPS coil 544 positioned inside.

During use of the catheter, the rotator core 520 rotates the drive shaft 530 which, in turn, rotates the imaging core 540. The electrical connector 600 inside of the rotator core 520 rotates while still maintaining electrical connection with a corresponding electrical connector attached to the motor drive unit.

The telescope 570 can be retracted and extended to move the position of the imaging core 540 inside the sheath. This allows the imaging core 540 to take images at different positions along the blood vessel while the sheath 580 remains stationary.

The above described implementation of the connector 100 in the context of a medical device is exemplary. As discussed above, other implementations are possible both within and outside of the medical device field. Additionally, other forms of catheters can implement the connector 100. The catheter described above was merely exemplary. For example, a catheter including a rotating ablation device can be electrically connected to a motor drive unit using the connector 100 or multi-pin connector 300 described.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus comprising:
    a connector that is configured to connect a motor drive unit to a catheter, the catheter being a tubular instrument that can be inserted into a body cavity or blood vessel, the connector including:
        a female portion, including one or more electrical contacts and a locking geometry, where the one or more electrical contacts are configured to mate to one or more electrical contacts of a male portion and the locking geometry is configured to mate to a corresponding locking geometry of the male portion; and
        a male portion, including one or more electrical contacts and a locking geometry, where the one or more electrical contacts are configured to mate to one or more electrical contacts of the female portion and the locking geometry is configured to mate to a corresponding locking geometry of the female portion,
    where the connector is configured to rotate such that when the female and male portions are mated, rotational movement from the motor drive unit is transferred to the catheter and an electrical connection is made between the motor drive unit and the catheter; and
    where the connector is a multi-pin connector and the male portion includes a plurality of pins and the female portion includes a plurality of corresponding apertures configured to receive the plurality of pins.

2. The apparatus of claim 1, where the locking geometry includes one or more keys in either the female or male portion and one or more corresponding grooves in the other portion.

3. The apparatus of claim 2, where the one or more keys are in the male portion and the one or more corresponding grooves are in the female portion.

4. The apparatus of claim 2, wherein the one or more keys comprise two keys on opposite sides of the male or female portion containing the one or more keys.

5. The apparatus of claim 2, wherein the number of keys equals the number of grooves.

6. The apparatus of claim 1, where:
    the catheter includes a rotator core, a drive shaft, and an imaging core; and
    the connector is positioned within the rotator core.

7. The apparatus of claim 1, where the connector conforms to the USB (Universal Serial Bus) electrical specification and protocol.

8. The apparatus of claim 1, further comprising the catheter coupled to the connector.

9. The apparatus of claim 8, where the catheter includes a rotator core, a drive shaft, and an imaging core; and the connector is positioned within the rotator core.

10. The apparatus of claim 8, wherein the catheter includes the male portion of the connector.

11. The apparatus of claim 1, further comprising the motor drive unit coupled to the connector.

* * * * *

UNITED STATES PATENT AND TRADEMARK OFFICE
CERTIFICATE OF CORRECTION

PATENT NO. : 7,530,953 B2 Page 1 of 1
APPLICATION NO. : 11/669752
DATED : May 12, 2009
INVENTOR(S) : E. Scott Harshman et al.

It is certified that error appears in the above-identified patent and that said Letters Patent is hereby corrected as shown below:

Title Page; item (73);
    In the Assignee, delete "Boston Scientific Neuromodulation Corporation" and insert -- Boston Scientific SciMed, Inc. --, therefor.

Signed and Sealed this

Twentieth Day of October, 2009

David J. Kappos
*Director of the United States Patent and Trademark Office*